United States Patent
Evans

[11] Patent Number: 5,955,655
[45] Date of Patent: Sep. 21, 1999

[54] REPLACEABLE TEST SPECIMENS FOR MACHINES ADAPTED TO TEST MATERIAL WEAR AND LUBRICATION PROPERTIES AND ASSOCIATED METHODS

[76] Inventor: Paul R. Evans, 5S342 Scott Rd., Big Rock, Ill. 60511

[21] Appl. No.: 08/908,895

[22] Filed: Aug. 8, 1997

[51] Int. Cl.⁶ .................................................. G01N 3/56
[52] U.S. Cl. ........................................................ 73/7
[58] Field of Search ................................. 73/7–10

[56] References Cited

U.S. PATENT DOCUMENTS

| | | |
|---|---|---|
| 1,188,789 | 6/1916 | Kass . |
| 2,106,170 | 1/1938 | Faville . |
| 2,110,288 | 3/1938 | Cornell . |
| 2,364,150 | 12/1944 | Lowenstein . |
| 2,812,457 | 11/1957 | Crawford . |
| 2,832,395 | 4/1958 | Fisher . |
| 2,932,995 | 4/1960 | Durfee . |
| 2,958,245 | 11/1960 | Neef . |
| 3,190,109 | 6/1965 | Faville . |
| 3,218,059 | 11/1965 | Andrew . |
| 3,998,445 | 12/1976 | Goltz . |
| 4,436,385 | 3/1984 | Fischer . |
| 4,445,678 | 5/1984 | George . |
| 4,861,010 | 8/1989 | Neil . |
| 4,893,802 | 1/1990 | Lin . |
| 4,923,186 | 5/1990 | Durfee . |
| 4,986,109 | 1/1991 | Moon .............................................. 73/7 |
| 5,060,920 | 10/1991 | Engibarov . |
| 5,343,733 | 9/1994 | Nakagawa et al. ............................ 73/7 |

FOREIGN PATENT DOCUMENTS 001677587  9/1991  U.S.S.R. ........................................ 73/7

*Primary Examiner*—Robert Raevis

[57] ABSTRACT

Opposing insert holders disposed on either side of a rotatable pin for use in a wear testing machine includes wear specimen inserts releasably secured in complimentary shaped cavities by selectively moving first wall portions of the cavity toward second wall portions.

27 Claims, 7 Drawing Sheets

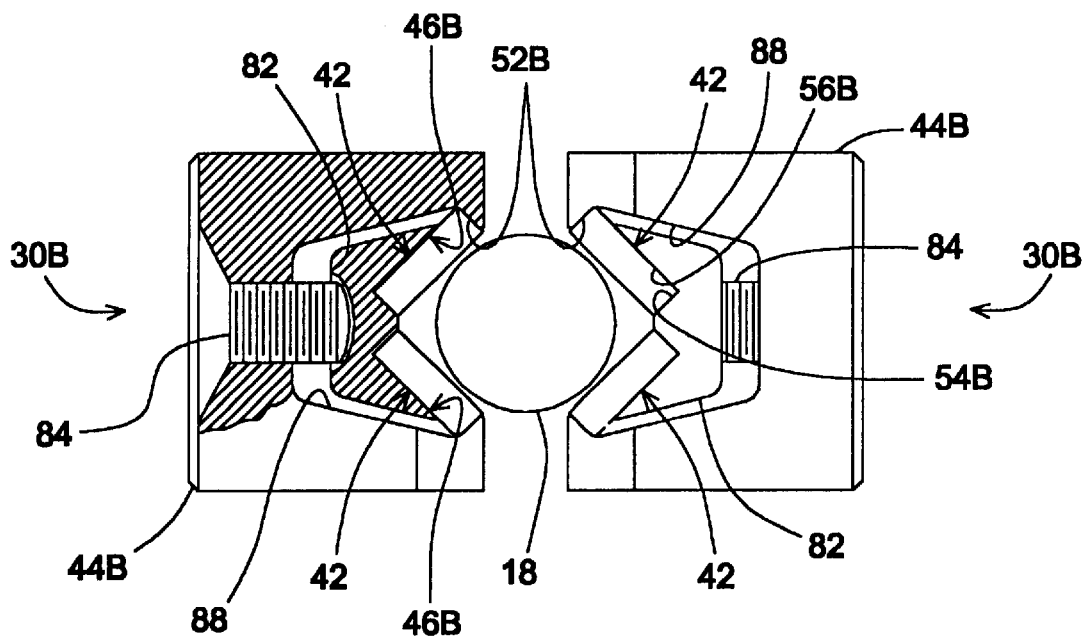
Fig 13
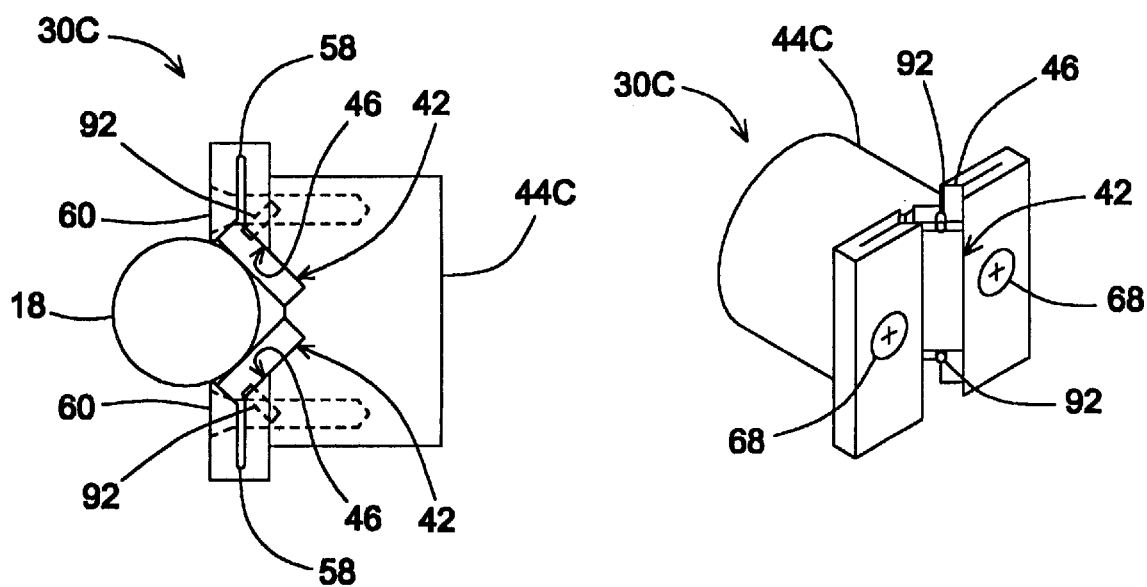
Fig 14
Fig 15

REPLACEABLE TEST SPECIMENS FOR MACHINES ADAPTED TO TEST MATERIAL WEAR AND LUBRICATION PROPERTIES AND ASSOCIATED METHODS

BACKGROUND OF THE INVENTION

This invention relates generally to machines adapted for testing lubrication and material wear properties. More specifically, the invention relates to machines of the type having wear specimens, also known as bearing blocks, disposed on either side of a rotating pin, and adapted to apply radial inwardly directed pressure onto the pin for wear and lubrication testing purposes.

One such test machine is disclosed in M. Cornell, U.S. Pat. No. 2,110,288, and certain associated test methods are disclosed in F. A. Faville, U.S. Pat. No. 2,106,170 and F. A. Faville, U.S. Pat. No. 3,190,109. Standardized tests for such machines are included in ASTM D 2670-88, Measuring Wear Properties of Fluid Lubricants; ASTM D 3233-93, Measurement of Extreme Pressure Properties of Fluid Lubricants; and ASTM D 2625-90, Endurance (Wear) Life and Load-Carrying Capacity of Solid Film Lubricants.

In machines of this general type, loading jaws or bearing block holders located on either side of the pin are formed with bores extending radially therefrom. A set screw is threaded into the outer ends of the bores, the bearing blocks are slidably received into the inner ends of the bores, and a load transferring ball is located between the set screw and the be ring block. The end of the bearing block adjacent the ball is formed with a conical depression or dimple for receiving the ball in axial compressive load carrying contact. The opposite end of the bearing blocks are formed with wear surfaces that define a V-shaped notch for receiving and establishing line bearing contact with the pin.

During testing, a force application mechanism moves the bearing block holders inwardly toward the pin. When the blocks are in contact with the rotating pin, the force from the mechanism is transferred from the bearing block holder to the bearing block via the ball in force transferring contact therewith. During such testing, the bearing surfaces of the V-shaped notch experience wear resulting from the pressure applied to the rotating pin by the bearing blocks. Therefore, prior bearing blocks of this type must typically be replaced after each test.

Studying the wear patterns and measuring the depth of wear on the bearing or wear surfaces of such prior bearing blocks presents difficulties because of the presence of the adjacent wear surface defining the V-shaped notch.

In addition, testing relatively soft materials with such prior bearing blocks presents difficulties. If the blocks are formed from the soft material, the block will likely undergo deformation due to compressive forces and the length of the material of the bearing block between the ball and the pin. With conventional testing machines, this compression will result in substantial changes in the force applied by the loading mechanism, and require careful vigilance of the operator to compensate for the loss in applied force. The outwardly directed force component due to the force transmitting relation of the ball acting against the angled surface of the conical depression in the bearing block results in further deformation of the specimen. Quit simply, prior bearing blocks made from soft materials will typically not hold their. shape sufficiently to provide meaningful wear data.

SUMMARY OF THE INVENTION

The general aim of the present invention is to provide new and improved apparatus for applying pressure to the rotating pin of conventional machines adapted to test material wear and lubrication properties, the apparatus being interchangeable with prior bearing blocks of such conventional machines.

A detailed objective is to achieve the foregoing by providing an insert holder adapted to carry replaceable wear inserts with contact bearing wear surfaces defining a substantially V-shaped notches when installed into the holder, thus eliminating the need and expense of replacing entire bearing blocks after each test.

Another detained objective of the invention is to provide means for easily installing, securing, and removing the inserts from the insert holders.

These and other objectives and advantages of the invention will become more apparent from the following detailed description when taken in conjunction with the accompanying drawings.

In one embodiment o f the invention, cavities sized to slidably receive inserts having substantially rectangular cross-sections are formed in the insert holders. Cap members resiliently connected to the holders are manually actuated for releasably securing the inserts into the cavities. A restriction and complimentary relief ensure that the inserts are installed into the holders with a predetermined surface facing outwardly for load bearing contact with the rotating pin of the test machine.

BRIEF DESCRIPTION OF THE DRAWINGS

FIGS. 12–21 are views of alternate embodiments of the present invention.

Figure 1:
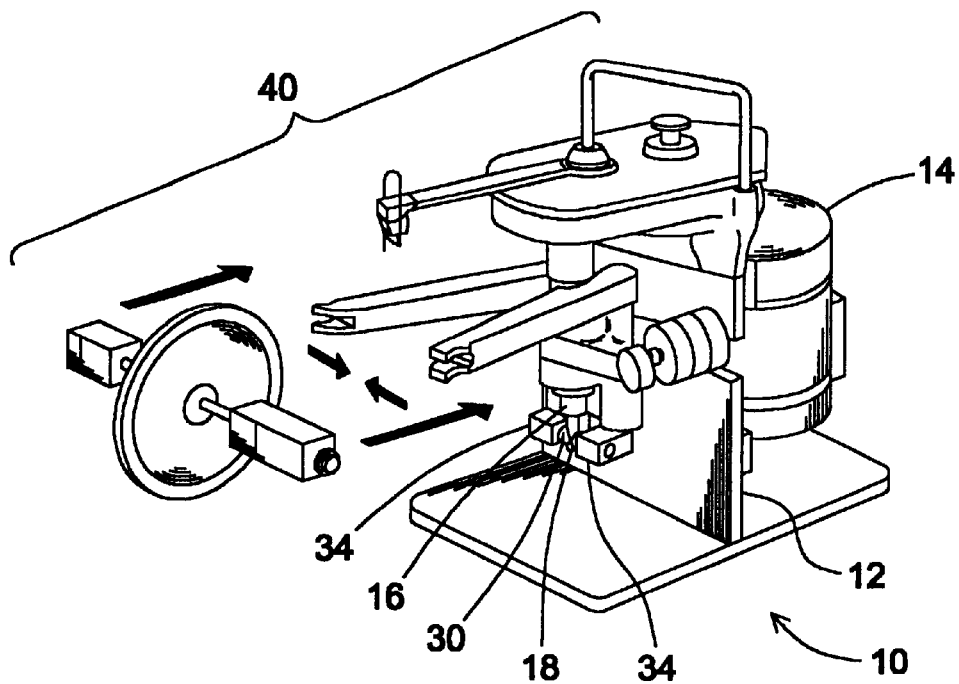
FIG. 1 is a view of a conventional wear testing machine having a rotating pin and opposing pressure applying apparatus of the type useful in connection with the present invention.
Figure 2:
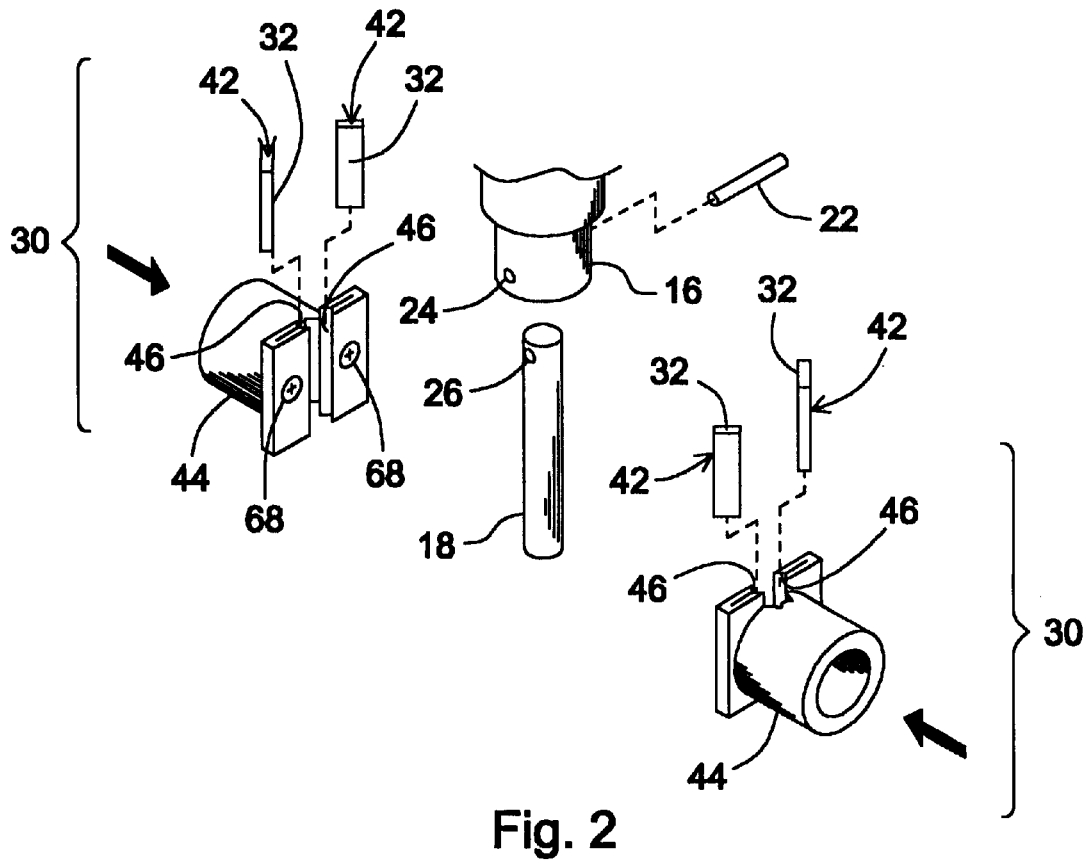
FIG. 2 is an enlarged exploded perspective view of certain parts of the machine of FIG. 1 and showing the unique aspects of the present invention.

While the invention is susceptible of various modifications and alternative constructions, certain illustrated embodiments have been shown in the drawings and will be described below in detail. It should be understood, however, that there is no intention to limit the invention to the specific forms disclosed, but on the contrary, the intention is to cover all modifications, alternative constructions, and equivalents falling within the spirit and scope of the invention.

DETAILED DESCRIPTION OF THE INVENTION

For purposes of illustration, the present invention is shown in the drawings in connection with a bench test machine 10 (FIG. 1) of the type adapted for use in testing material and lubricant wear properties such as disclosed in M. Cornel, U.S. Pat. No. 2,110,288. The construction and operation of such machines is well known, and will therefore be discussed herein only to the extent needed for understanding of the present invention.

Figure 3:
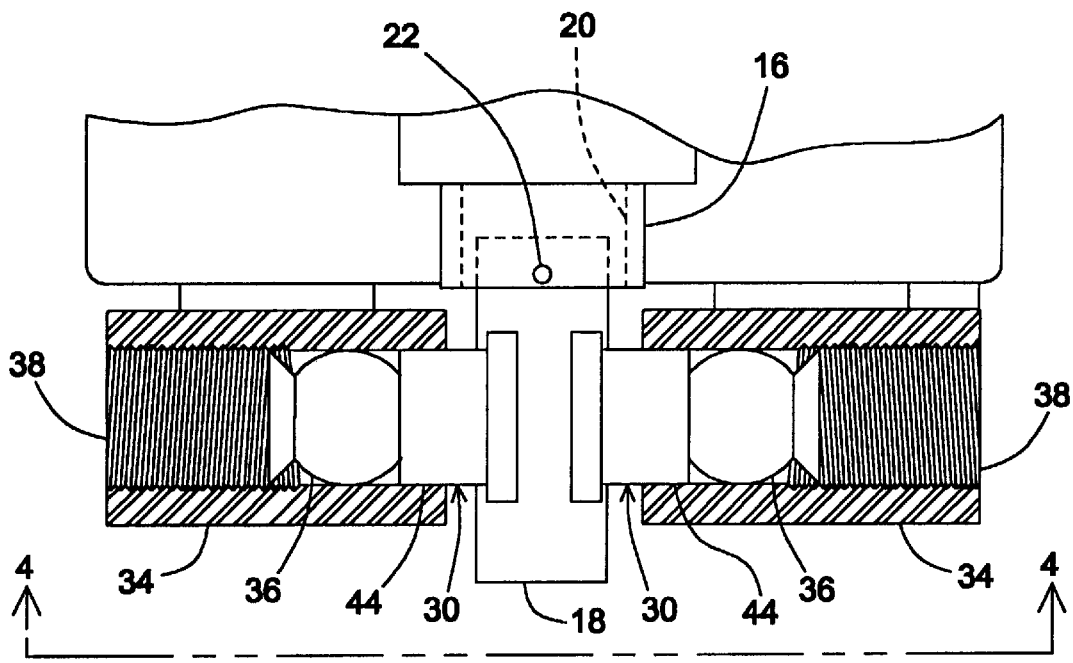
FIG. 3 is an enlarged fragmentary view of the parts of FIG. 2 as assembled in the machine of FIG. 1.

The machine 10 includes a frame structure 12 and an electric motor 14 operably connected to a collar 16 for rotation about a predetermined axis. Bearing pin 18 is slidably received into opening 20 (FIG. 3) formed in the collar, and is secured therein with shear pin 22 slidably extending through a transverse opening 24 formed through the collar and through an aligned transverse opening 26 formed through the upper end portion of the bearing pin. Wear specimens include wear surfaces 32 which define substantially V-shaped notches facing one another for receiving the bearing pin 18 therebetween.

Figure 4:
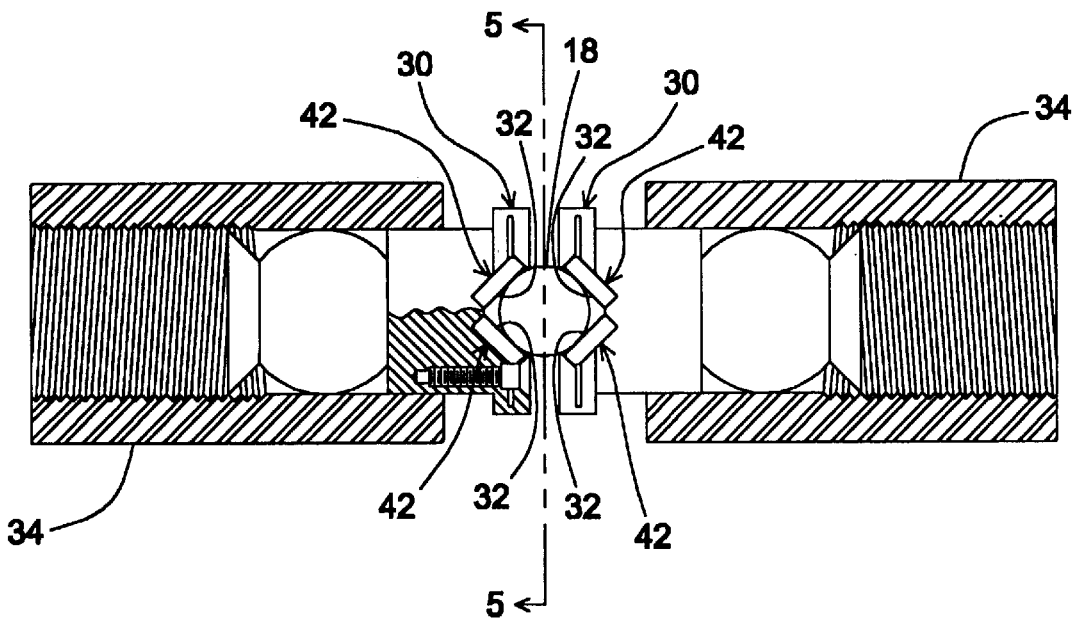
FIG. 4 is a fragmentary view taken substantially along the line 4—4 of FIG. 3.
Figure 5:
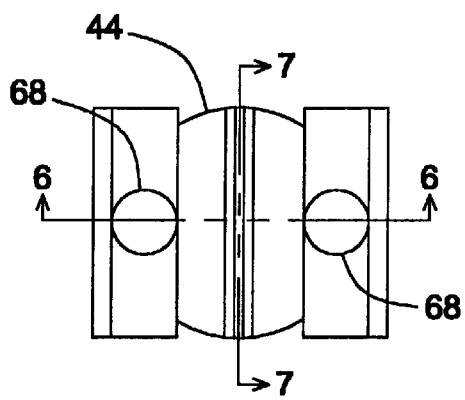
FIG. 5 is a side view of a certain part shown in FIG. 2.

During normal operation of the machine 10, i.e., during a typical wear test, the bearing pin 18 is rotated by the electric motor 14 and a load applying mechanism 40 (FIG. 1) moves the wear specimens toward one another, resulting in line-bearing pressure or frictional contact between the stationary bearing surfaces 32 and the rotating bearing pin (see FIG. 4). It is noted that, although "line-bearing" pressure of contact is referred to herein, genuine "line" contact ceases and slight area contact results as soon as the bearing surfaces begin to wear.

In accordance with the present invention, insert holder assemblies 30 include insert holders 44 adapted to releasably carry wear specimen inserts 42, the wear surfaces 32 being formed on the inserts 42 and being oriented to define the generally V-shaped notches for receiving the bearing pin 18 therebetween. The insert holder assemblies are operably connected to the load applying mechanism 40 for applying contact pressure between the bearing pin and the surfaces 32 of the inserts in a conventional manner. The inserts are preferably of a simple geometry for ease of manufacture and reduced cost as compared with prior bearing block wear specimens having integral wear surfaces. As a result, the less expensive inserts 42 may be replaced after each test rather than replacing entire bearing blocks of prior arrangements such as disclosed in M. Cornell.

Figure 6:
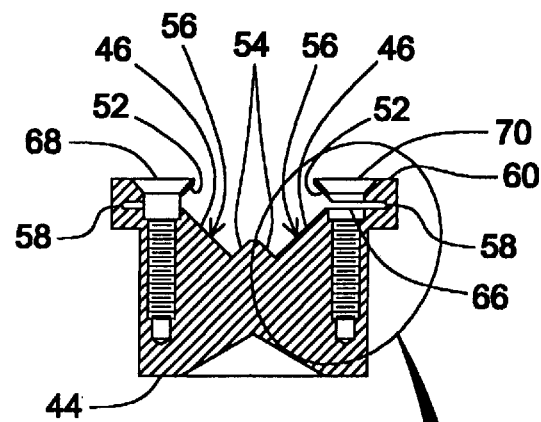
FIGS. 6 and 7 are cross-sectional views taken substantially along the lines 6—6 and 7—7, respectively, of FIG. 5.
Figure 7:
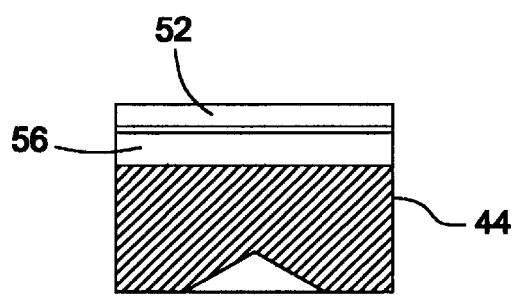
Figure 9:
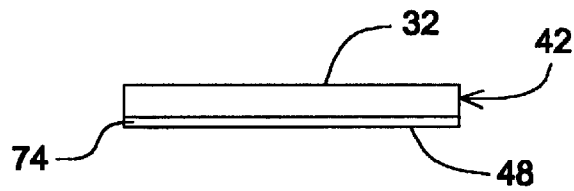
FIGS. 9–11 are orthogonal views of another part shown in FIG. 2.
Figures 10, 11:
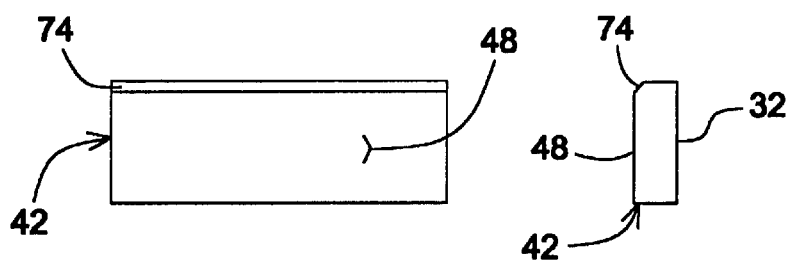
Figure 12:
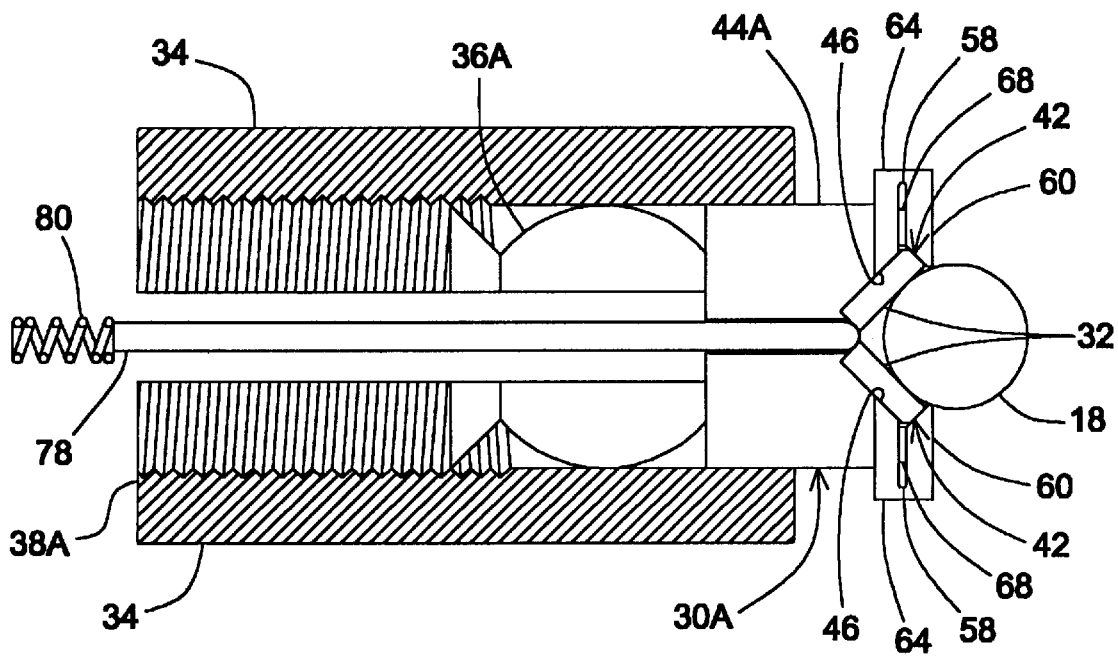
Figure 21:
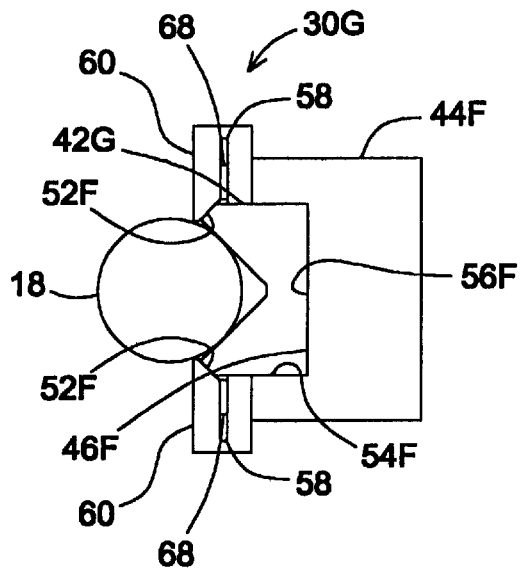
Figure 20:
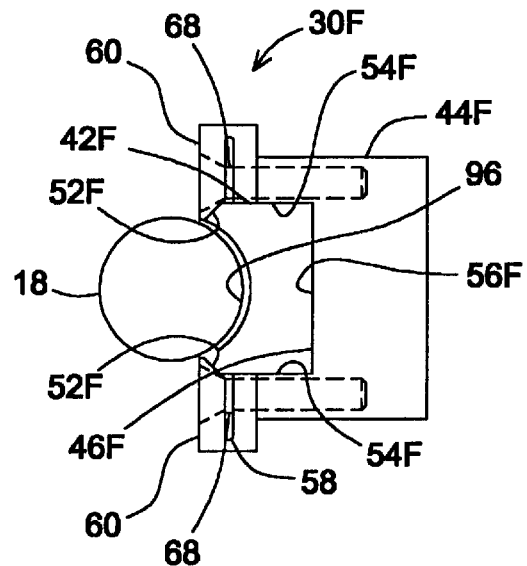
Figure 16:
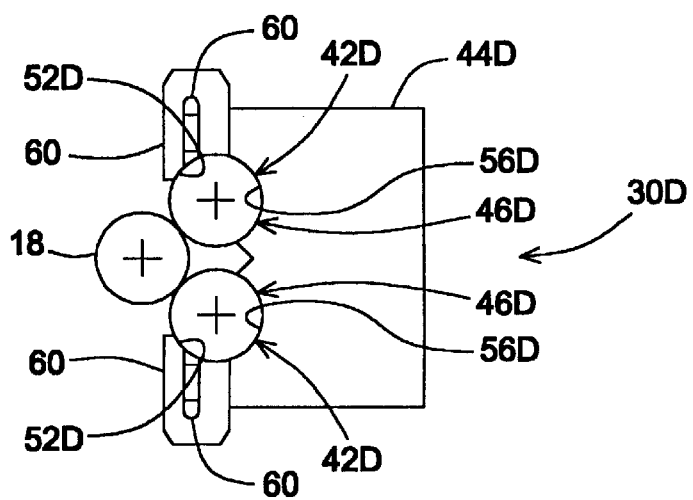

More specifically, the insert holder assemblies 30 are slidably carried in loading jaws 34 (FIG. 3), with a ball 36 and a set-screw 38 located in each loading jaw to limit radial outwardly movement of the insert holder assemblies. The inserts 42 are generally flat, relatively thin bars with a substantially rectangular cross-section, and having oppositely facing surfaces 32 and 48 (FIGS. 9–11). The inserts are received into substantially rectangular slots or cavities 46 (FIG. 6) formed in the insert holders 44, the cavities being generally defined by opposing side wall portions 52 and 54, and base wall portion 56 (see e.g., FIG. 8) and extending axially relative to the bearing pin 18.

Advantageously, the absence of material adjacent the edges of the surfaces 32 and 48 enables those surfaces to be easily manufactured to a relatively fine finish on, for example, a flat honing surface plate. Such an operation is not possible with the "connected" V-shaped wear surfaces of prior bearing blocks. Thus, the wear surface of the insert 42 may be manufactured with a more consistent surface finish at the same or at a reduced cost when compared with forming the wear surfaces on prior bearing blocks. In addition, since the mass of the insert 42 is substantially less than the mass of prior bearing blocks, greater accuracy is possible when comparing weight loss measurements to determine loss of material due to specimen wear.

In keeping with the invention, the insert holder 44 includes means for releasably clamping the inserts 42 into the slots 46, the clamping means preferably being adapted such that all parts remain connected to the insert holder to preclude the possibility of losing parts when changing inserts.

More specifically, a slot 58 (FIG. 8) is formed extending from the cavity 46 into the insert holder 44, and manually operable means are provided for selective opening and closing the leading edge portion of the slot to cause movement of at least a portion of one of the side wall portions 52 or 54 toward and away from the other side wall portion, increasing and decreasing, respectively, the size or width of the cavity 46 for selectively capturing the insert 42 therein.

Figure 8:
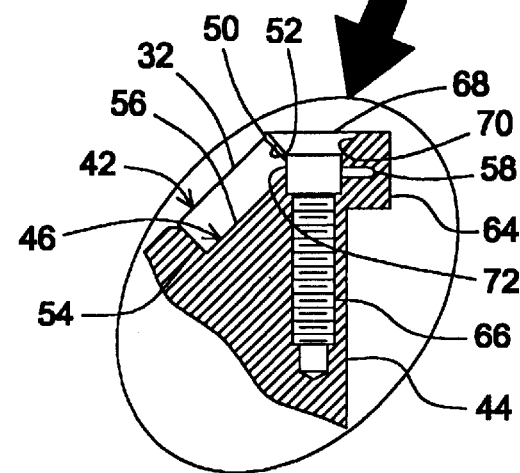
FIG. 8 is as enlarged fragmentary cross-sectional view of a portion of the part shown in FIG. 6.

In the embodiment shown, the slot 58 extends from and along the length of the outer internal corner portion of the cavity 46, defining a lever portion 60 (FIG. 6) and an integral interconnecting spring portion 64 (FIG. 8). An opening 66 threaded to engage screw 68 extends from the slot 58 into the insert holder 44, and a second opening 70 sized to slidably receive the threaded screw 68 is formed through the lever portion 60. With this arrangement, the slot decreases in width as the screw is turned into the opening 66 and the head of the screw engages the lever portion 60. When the screw 68 is then turned outwardly, the lever portion resiliently returns outwardly to an "open" position, increasing the width of the cavity 46 and resulting in a small gap between the insert 42 and a side wall portion such as indicated at 50 (FIG. 8). With the cavity 46 sized to slidably receive the insert 42 when the screw 68 is turned outwardly, and with the lever portion 60 adapted to clamp the insert against the side wall portion 54 opposite the lever portion when the screw is turned inwardly, the screw and lever portion are operable to selectively clamp the insert 42 into the insert holder.

The cavity 46 and insert 42 may be adapted to insure that only the surface 32 is available for wear testing. In this instance, either the cavity or the insert may be formed with a guiding shape extending outwardly from a respective adjacent surface, with the other being formed with a complimentary shaped or recess for slidably receiving the protruding guiding shape.

In the embodiment shown, the screw 68 is formed with a collar portion 72 (FIG. 8) that extends into the adjacent corner of the cavity 46 to define a guiding shape therein and partially blocking clear passage of the insert 42 in that corner. The insert is formed with a complimentary chamfer 74 (FIG. 11) along one corner such that the insert will fit into the cavity only if the chamfered corner is adjacent the collar 72. If the insert is installed into the cavity with any of the other corners in that position, the collar will prevent the corner from passing by and thus prevent the insert from being fully installed in that orientation. Such an embodiment is especially useful if the wear surface 32 is to be formed or treated with special surface or finish. Moreover, it is apparent that the guiding shape could be alternately configured within the scope of the present invention to insure that the face 32 is faces outwardly when the insert is installed into the holder 44 for engaging the rotating pin 18.

Alternately, if the surfaces 32 and 48 are both finish machined, the insert 42 may be installed with either of these surfaces facing outwardly to function as the wear surface by providing a screw 68 without the collar 72. For certain tests, such an arrangement enables the inserts to be flipped over and used for two tests before replacement is necessary, further reducing the cost of conducting those tests.

Advantageously, the geometry of inserts 42 provides improved dimensional stability as compared with prior bearing blocks for wear specimens made from soft materials because the material load-bearing thickness is substantially less and the inserts are substantially confined within the slot 46. As a result, the repeatability of testing such soft materials will be enhanced with the use of inserts 42.

FIGS 12 through 21 depict alternate embodiments of the invention including alternate insert holder assemblies. These embodiments are briefly described below, with features equivalent or comparable to features of the embodiment previously described being identified with the same item number, but having a letter modifier added.

In an alternate embodiment (FIG. 12), set screw 38A, ball 36A, and insert holder 44A are formed with aligned axially extending openings adapted to receive a temperature sensing thermocouple 78. A spring 80 lightly biases the thermocouple toward the inserts 42 insures that thermal conductive surface contact is maintained between the thermocouple and the inner edge faces of the inserts 42.

In another alternate embodiment (FIG. 13), the insert holder assembly 30B includes a set screw 84 and a back plate 82 adapted to releasably clamp the inserts 42 into the insert holder 44B. The back plate is received into an axially extending cavity 88 in the holder, the cavity 88 being sized to allow for movement of the back plate toward and away from the bearing pin 18. The side wall portion 52B is defined on the holder 44B, and the back wall portion 56B and side wall portion 54B are defined in one end of the back plate. The set screw 84 slidably and rotatably engages the opposite end of the back plate and is threaded into the holder for driving the back plate toward the side wall portions 52B, thus decreasing the size of the cavities 46B and clamping the inserts therein. Backing the set screw 84 out releases the inserts for removal from the holder. The back plate is generally captured in the cavity 88 by complimentary surfaces of the end of the screw and the back plate. However, the back plate may be removed from the holder for Cleaning by backing the set screw 84 further after releasing the inserts.

In the embodiment shown in FIGS. 14 and 15, means such as pins 92 are provided near the ends of the cavities 46 for positioning the inserts 42 therein. Specifically, the pins 92 extend from the holder 44C and into the cavity 46 such that the inserts 42 may be slipped into the slot when the screw is backed out, allowing the lever portion into its outward release position, but are captured longitudinally in the slot.

A still another alternate embodiment (FIG. 16), the inserts 44D are generally cylindrical members, and the cavities 46D are formed with curved wall portions 52D, 56D adapted for selective relative movement toward and away from one another by turning screw 68 in and out, respectively. In this instance the cylindrical inserts are releasably secured into the insert holder so as to extend parallel with the bearing pin, and the centers of the inserts are concentric with the center axis of the pin 18, such that the inserts 42D present axially extending line-bearing contact surfaces for engagement with the rotating pin.

Figure 17:
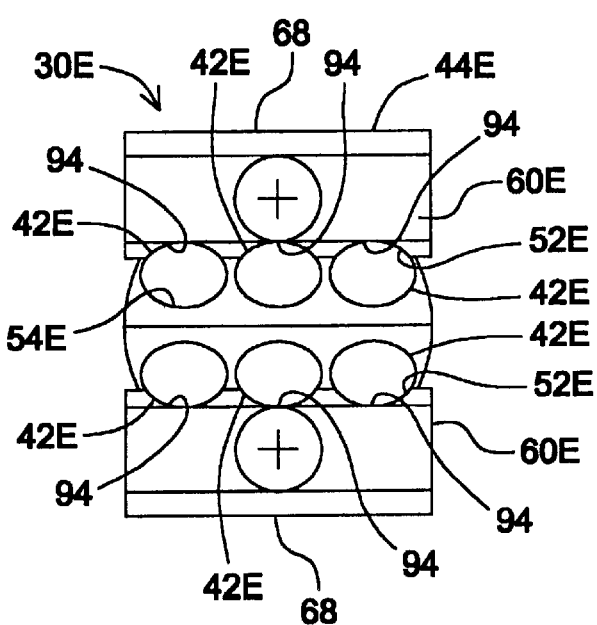
Figure 18:
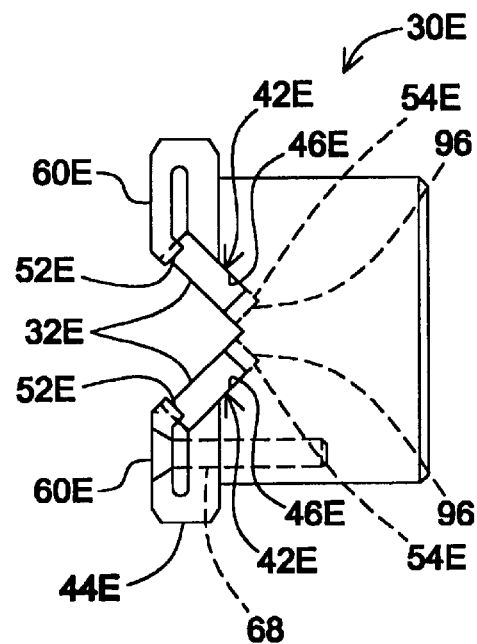
Figure 19:
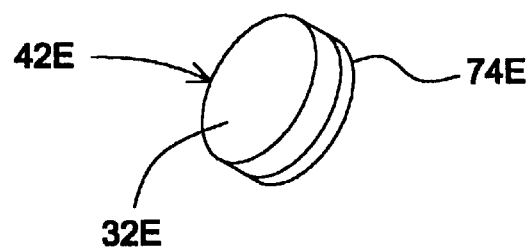

In the embodiment shown in FIGS. 17–19, the insert holder 44E is adapted to releasably carry three button inserts on each side of the V-shaped notch, the inserts being spaced apart from one another in the cavities. The inserts are received into complimentary shaped openings 94, the openings 94 on one side of the holder being connected together such that the lever portion 60E is operable to clamp or release the inserts in the holder with the screw 68. The buttons shown are provided with a chamfer 74E to engage complimentary surface 96 to ensure that surface 32E faces outwardly to engage the bearing pin 18.

The insert 42F (FIG. 20) is adapted for modified testing conditions by presenting a curved contact surface 96 for circumferentially extending engagement with the bearing pin 18. The modified testing with such curved-bearing contact surfaces is typically conducted with less force applied by the load mechanism 40. In this instance, one insert 42F is carried in each of the two opposing holders 44F. As in the previously described embodiments, lever portions 60 resiliently bend toward opposing side wall portions 54F and back wall portion 56F to engage and trap the insert 42F in the slot 46F as the screw 68 is tightened, and the lever portions resiliently return in the opposite direction to a release position for a sliding fit between the insert and the slot when the screw is loosened. Advantageously, the holder 44F may releasably carry insert 42G which is formed with a V-shaped notch for line-bearing contact with the bearing pin 18 as earlier described. Thus, it will apparent to one skilled in the art that these and additional embodiments remain within the scope of the present invention.

From the foregoing, it is clear that the present invention brings to the art new and unique apparatus for use in lubrication and wear testing machines 10. Specifically, holders formed with cavities or slots having wall portions that are selectively moveable between clamping and release positions with respect to other wall portions of the slots allows wear specimen inserts to be easily installed, secured, and removed therefrom. This arrangement permits the use of wear specimens that are less expensive to manufacture when compared with prior bearing block wear specimens, and allows wear testing on alternate configuration specimens that was not previously available. Moreover, the present invention enables enhanced ease of and greater accuracy in conducting visual and weight inspections of the insert specimens for wear.

I claim:

1. A machine comprising:
    a generally cylindrical pin;
    means for rotating said pin;
    a pair of holders disposed on either side of said pin, said holders having a plurality of generally inwardly opening cavities, each of said cavities having first and second wall means;
    insert means in said cavities;
        said holders being connected for movement toward and away from said pin to effect and disengage, respectively, force transmitting relation between said insert means and said pin; and
        means for selectively moving one of said wall means with respect to the other of said wall means to selectively clamp said inserts into said cavities.

2. A machine as defined in claim 1 in which force transmitting relation extends generally circumferentially around said pin.

3. A machine as defined in claim 1 in which said insert means presents a substantially line-bearing force transmitting relation extending generally axially with said pin.

4. A machine as defined in claim 3 in which said insert means define a generally V-shape notch for substantially enclosing said rotating pin.

5. A machine as defined in claim 1 in which said one wall means is resiliently connected to said holder for movement between clamping and release positions.

6. A machine as defined in claim 5 in which said one wall means is located outwardly of said other wall means with respect to said pin.

7. A machine as defined in claim 6 in which said moving means includes a threaded member operably connected between said one wall means and said holder.

8. A machine as defined in claim 1 in which each of said holders includes at least two cavities.

9. A machine as defined in claim 1 further comprising thermocouple means having a temperature sensing portion resiliently biased into surface contact with said insert means.

10. A machine as defined in claim 1 in which said insert means includes a predetermined surface adapted for force transmitting contacting relation with said pin, said machine further comprising first guiding means connected to said holder and said insert means including second guiding means cooperatively associated with said first guiding means such that only said predetermined surface is presented for said contacting relation.

11. A machine comprising:
   a generally cylindrical pin;
   means for rotating said pin;
   a pair of holders disposed on either side of said pin;
   two pair of inserts disposed on either side of said pin;
      said holders being connected for movement toward and away from said pin to effect and disengage force transmitting relation between said inserts and said pin; and
   means for releasably connecting a pair of inserts to each of said holders.

12. A machine as defined in claim 11 in which said inserts present substantially line-bearing force transmitting relations extending generally axially with said pin.

13. A machine as defined in claim 12 in which each of said pairs of inserts define a generally V-shaped notch for receiving said rotating pin therebetween.

14. A machine as defined in claim 11 in which connecting means includes spring means integrally connected to said holders and selectively moveable between clamping and release positions.

15. A machine as defined in claim 14 in which said connecting means further includes threaded means operably connected between said holder and said integral spring means for effecting movement between said positions.

16. A machine as defined in claim 11 in which said holders are formed with a pair of cavities sized to slidably receive said inserts, said connecting means being adapted to releasably secure said inserts in said cavities.

17. A machine as defined in claim 16 in which said cavities are substantially rectangular having first and second generally opposing side walls, and in which said connecting means includes means for selectively moving one of said side walls toward and away from the other of said side walls for selectively clamping and releasing, respectively, said inserts.

18. A machine as defined in claim 17 in which said moving means is resiliently connected to said body.

19. A machine as defined in claim 11 further comprising means for restricting movement of said inserts axially with respect to said pin.

20. A method for testing lubrication, friction and material wear between two relatively moving surfaces, said method comprising the steps of:
   (A) providing apparatus equipped with:
      (i) a pin member,
      (ii) means for rotating said pin member,
      (iii) two pair of wear specimens, each pair being disposed on either side of said pin member, and
      (iv) means for simultaneously moving said wear specimens toward and away from said pin member;
   (B) rotating said pin member; and
   (C) moving said wear specimens into simultaneous engagement with said rotating pin member to enable testing of said properties.

21. A method as defined in claim 20 in which said wear specimens are releasably connected to said apparatus, said method further comprising the steps of:
   (D) removing said wear specimens from said apparatus; and
   (E) providing and installing a second two pair of wear specimens into said apparatus for additional testing.

22. A method as defined in claim 20 further comprising the steps of:
   (D) providing:
      (i) a pair of jaws movably disposed on either side of said pin member,
      (ii) a pair of holders connected to said jaws for movement therewith, said holders each having a body and having inner and outer wall means defining a pair of channels opening generally toward said pin member for carrying said wear specimens,
         one of said inner and outer wall means being connected to said body for movement between (a) a clamping position for clamping said wear specimens in said channels and (b) a release position for slidably receiving and releasing said wear specimens from said channels, and
      (iii) threaded means operatively connected between said body and said one wall means for rotational movement in first and second directions for effecting movement of said one wall means between said clamping and release positions,
         said wear specimen moving means being operatively connected to said jaws for moving said wear specimens;
   (E) clamping said wear specimens in said holders prior to said moving step by turning said threaded means in said first direction; and
   (F) releasing said wear specimens from said holders after completion of a test by turning said threaded means in said second direction.

23. A method as defined in claim 22 in which said one wall means is resiliently connected to said body and is resiliently biased toward said release position, and in which said threaded means is threaded into said body and slidably engaging said one wall means to effect movement of said one wall means toward said clamping position by turning said threaded means into said said body.

24. A method for testing lubrication, friction and material wear between two relatively moving surfaces, said method comprising the steps of:
   (A) providing apparatus equipped with:
      (i) a pin member,
      (ii) means for rotating said pin member,
      (iii) a pair of jaws movably disposed on either side of said pin member,
      (iv) means for simultaneously moving said jaws toward and away from said pin member;
      (v) a pair of holders slidably connected to said jaws for movement therewith, said holders being disposed on either side of said pin member between said jaws and said pin member, and
      (vi) a pair of wear specimens releasably connected to said holders for movement therewith, said wear specimens being disposed between said holders and said pin member;
   (B) rotating said pin member; and
   (C) moving said jaws toward said pin member for simultaneous engagement between said wear specimens and said rotating pin member to enable testing of said properties.

25. A method as defined in claim 24 further comprising the steps of:
   (D) removing said wear specimens from said apparatus;
   (E) providing and installing a second pair of wear specimens into said apparatus for additional testing.

26. A method as defined in claim 24 further comprising the steps of:
   (D) providing:
      (i) said holders each having a body and having inner and outer wall means defining channel means opening generally toward said pin member for carrying one of said wear specimens,
         one of said inner and outer wall means being connected to said body for movement between (a) a clamping position for clamping said wear specimens in said channels and (b) a release position for slidably receiving and releasing said wear specimens from said channels, and
      (ii) threaded means operatively connected between said body and said one wall means for rotational movement in first and second directions for effecting movement of said one wall means between said clamping and release positions,
         said wear specimen moving means being operatively connected to said jaws for moving said wear specimens;
   (E) clamping said wear specimens in said holders prior to said moving step by turning said threaded means in said first direction; and
   (F) releasing said wear specimens from said holders after completion of a test by turning said threaded means in said second direction.

27. A method as defined in claim 26 in which said one wall means is resiliently connected to said body and is resiliently biased toward said release position, and in which said threaded means is threaded into said body and slidably engaging said one wall means to effect movement of said one wall means toward said clamping position by turning said threaded means into said bodies.

* * * * *